United States Patent [19]

Hutsell

[11] Patent Number: 5,482,925
[45] Date of Patent: Jan. 9, 1996

[54] COMPLEXES OF NITRIC OXIDE WITH CARDIOVASCULAR AMINES AS DUAL ACTING CARDIOVASCULAR AGENTS

[75] Inventor: Thomas C. Hutsell, North Oaks, Minn.

[73] Assignee: Comedicus Incorporated, Long Lake, Minn.

[21] Appl. No.: 210,043

[22] Filed: Mar. 17, 1994

[51] Int. Cl.$^6$ .......................... A61K 38/08; A61K 38/16; A61K 38/17; A61K 38/31

[52] U.S. Cl. .................................. 514/11; 514/2; 514/21; 514/56; 514/565; 530/300; 530/311; 530/316; 530/350; 530/855; 536/21; 562/560

[58] Field of Search ................................... 514/2, 11, 21, 514/56, 565; 530/300, 311, 316, 350, 855; 536/21; 562/560

[56] References Cited

U.S. PATENT DOCUMENTS

| 4,954,526 | 9/1990 | Keefer .................................... | 514/611 |
| 5,039,705 | 8/1991 | Keefer et al. ........................... | 514/611 |
| 5,155,137 | 10/1992 | Keefer et al. ........................... | 514/611 |

OTHER PUBLICATIONS

Ignarro et al., "Endothelium—derived nitric oxide: actions and properties," FASEB Journal, vol. 3, No. 1 Jan. 1989, pp. 31–36.
Toxicology and Applied Pharmacology, 91, 429–438 (1987), "Red Blood Cells Generate nitric Oxide from Directly Acting, Nitrogenous Vasodilators", by Harriet Kruszyna et al.
The Journal of Pharmacology and Experimental Therapeutics, vol. 218, No. 3, 1981, "Mechanism of Vascular Smooth Muscle Relaxation by Organic Nitrates, Nitrites, Nitroprusside and Nitric Oxide: Evidence for the Involvement of S–Nitrosothiols as Active Intermediates", by Ignarro et al., pp. 739–749.
J. Am. Chem. Soc., vol. 83, pp. 1819–1822 (1961), "The Reaction of Nitrogen(II) Oxide with Various Primary and Secondary Amines", by Russell S. Drago et al.
Nature, vol. 327, pp. 524–526, (1987), "Nitric Oxide Release Accounts for the Biological Activity of Endothelium–derived Relaxing Factor", by Palmer et al.
Arteriosclerosis, vol. 10, No. 6, (1990), pp. 966–990, "Regulation of Differentiated Properties and Proliferation of Arterial Smooth Muscle Cells", by Thyberg et al.
Journal of American College of Cardiology, vol. 17, No. 6, (1991), pp. 132B–136B, "Peptide Inhibition of Myointimal Proliferation by Angiopeptin, a Somatostatin Analogue", by Lundergan et al.
Transplantation Proceedings, vol. 21, No. 4, (1989), pp. 3686–3688, "Peptide Inhibition of Myointimal Proliferation Following Angioplasty in Rabbits", by Conte et al.
Platelets in Biology and Pathology, (1976), pp. 23–60, Chapter 2, "Adhesion and Aggregation: Morphological Demonstration and Quantitation In Vivo and In Vitro", by Baumgartner et al.
Annual Review of Pharmacology and Toxicology, vol. 24, (1984), pp. 175–197, "The Role of Endothelium in the Responses of Vascular Smooth Muscle to Drugs" by Furchgott.
Journal of the American College of Cardiology, vol. 15, No. 2, (1990), pp. 419–425, "Primary Peripheral Arterial Stenoses and Restenoses Excised by Transluminal Atherectomy: A Histopathologic Study", by Johnson et al.
The American Journal of Cardiology, vol. 60, pp. 20B–28B, "Role of Platelets and Thrombosis in Mechanisms of Acute Occlusion and Restenosis after Angioplasty", by Laurence Harker, (1987).
Biochemical Pharmacology, vol. 38, No. 7, (1989), pp. 1709–1715, "Biosynthesis of Nitric Oxide from L–Arginine: A Pathway for the Regulation of Cell Function and Communication", by Moncada et al.
Circulation Research, vol. 56, (1985), pp. 139–145, "Significance of Quiescent Smooth Muscle Migration in the Injured Rat Carotid Artery", by Clowes et al.
Circulation Research, vol. 46, (1980), pp. 625–634, "Inhibition of Rat Arterial Smooth Muscle Cell Proliferation by Heparin", by Guyton et al.
Circulation, vol. 79, No. 3, (1989), pp. 657–665, "Effects of Thrombin Inhibition on the Development of Acute Platelet–Thrombus Deposition During Angioplasty in Pigs", by Heras et al.
The Journal of Clinical Investigation, vol. 75, No. 5, (1985), pp. 1914–1918, "Evidence for a Functional Role of Endogenously Produced Somatomedinlike Peptides in the Regulation of DNA Synthesis in Cultured Human Fibroblasts and Porcine Smooth muscle Cells", by Clemmons et al.
Proceedings of the National Academy of Sciences, vol. 87, No. 13, (1990), pp. 5193–5197, "An L–Arginine/Nitric Oxide Pathway Present in Human Platelets Regulates Aggregation", by Radomski et al.
Nature, vol. 265, (1977), "Suppression by Heparin of Smooth Muscle Cell Proliferation in Injured Arteries", by Clowes et al., pp. 625–626.

Primary Examiner—Peter O'Sullivan
Attorney, Agent, or Firm—Merchant, Gould, Smith, Edell, Welter & Schmidt

[57] ABSTRACT

Novel complexes of nitric oxide (NO) and amines are described where the amine is a known cardiovascular agent having at least one or more primary or secondary amino groups and whereby the resulting complex is capable under physiological conditions of releasing in vivo dual active ingredients, the NO and the known cardiovascular agent. The complexes are used for treating cardiovascular diseases and for the prophylactic or therapeutic treatment of restenosis.

8 Claims, No Drawings

COMPLEXES OF NITRIC OXIDE WITH CARDIOVASCULAR AMINES AS DUAL ACTING CARDIOVASCULAR AGENTS

FIELD OF INVENTION

The present invention is concerned with novel complexes of nitric oxides with amines derived from known cardiovascular agents which, under physiological conditions, release nitric oxide and the corresponding cardiovascular amine providing dual activity in treating cardiovascular diseases and, particularly, in prophylactically and/or therapeutically treating restenosis.

BACKGROUND OF THE INVENTION

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann, *Rev. Pharmacol. Toxicol.* 24, 175–197, 1984). Recently, Palmer et al. have shown that EDRF is identical to the simple molecule, nitric oxide (NO) (*Nature* 317, 524–526, 1987). It has been hypothesized for years that many nitrovasodilators that mimic the effect of EDRF, like glyceryl trinitrate, amyl nitrite, $NANO_2$, and sodium nitroprusside (SNP), do so by virtue of their conversion to a common moiety, namely NO, which is also a vasodilator. (See Kruszyna et al., *Tox. & Appl. Pharmacol.* 91, 429–438, 1987; Ignarro, *FASEB J.* 3, 31–36, 1989; Ignarro et al., *J. Pharmacol. Exper. Therapeutics* 218 (3), 739–749, 1981).

Keefer et al. in U.S. Pat. Nos. 4,954,526, 5,039,705 and 5,155,137 describe primary amine, secondary amine and polyamine NO complexes, their methods of preparation and a method of treating cardiovascular disorders in mammals by administering such complexes to mammals in need thereof. These patents are expressly incorporated herein by reference.

Keefer et al. have recently reported that the above NO complexes may be particularly of use in prophylactically and/or therapeutically treating restenosis in a copending U.S. patent application.

Restenosis is characterized by three mechanistically distinct events: (1) in certain patients, an elastic recoil phenomenon which leads to abrupt closure of vessels within minutes to hours after the balloon angioplasty, (2) early (within two days of balloon injury) platelet aggregation and thrombus formation and (3) late (about two weeks after balloon injury) smooth muscle cell proliferation.

The elastic recoil phenomenon represents the relaxation of the over-stretched vessel segment. Recent observations [Johnson et al., *J. Am. Coll. Cardio.* 17:419–425, 1990] derived from microscopic examination of atherectomy specimens suggest that this mechanism may occur in up to 25% of angioplasty procedures classified as successful based on the initial angiogram. One possible explanation for this is that endothelial cells are destroyed in the angioplasty procedures; this endothelial cell dysfunction may result in vasospasm. Endotheliumderived relaxing factor (EDRF) has been shown to mediate the control of vascular tone and, thus, may be involved in this vasospasm. Since EDRF has been shown to be identical to nitric oxide [Palmer et al., *Nature* 317:524–526, 1987], it is reasonable to expect that nitric oxide may replace the EDRF functionality lost when the endothelial cells are destroyed during balloon angioplasty and, thus, prevent the acute closure of vessels.

Within minutes after vessel injury, platelet aggregates and fibrin with entrapped red blood cells are formed [Harker, *Am. J. Cardiol.* 60:21B-28B, 1987]. These thrombi contain attractants and mitogens for smooth muscle cells. Platelets adhering to the subendothelial surface are largely responsible for the mitogenic activity occurring during this phase of restenosis [Baumgartner and Muggil, in Gordon (ed): *Platelets in Biology and Pathology*, pp. 23–60, 1976]. Experimental data in animal models mentioned below clearly show the effectiveness of nitric oxide in preventing the aggregation and adhesion of platelets both in vitro and in vivo. It is, thus, reasonable to expect that these same activities will occur when nitric oxide is delivered to the site of vessel injury in mammals.

Smooth muscle cells, probably in response to release of mitogens from injured platelets described above, enter the growth cycle between two and three days after balloon injury and the vast majority of proliferation is completed within seven days [Clowes and Schwartz, *Circ. Res.* 56: 139–145, 1986]. It is probable that the proliferation of these smooth muscle cells leads to the restenosis observed in one-third to one-half of patients undergoing initial balloon angioplasty. Experimental data described below from in vitro model systems using rat- and human-aorta-derived smooth muscle cells clearly indicates that nitric oxide at concentrations approximating 20–100 $\mu M$ inhibit by 50% the rate of smooth muscle cell proliferation. Thus, nitric oxide delivered to the site of vessel injury at higher concentrations, e.g., in the range of 200–500 $\mu M$, for periods up to about seven days can reasonably be expected to be of prophylactic and/or therapeutic value in restenosis and related conditions.

Although many approaches to ameliorating restenosis have been tried in the past, these approaches have focused on only one primary intervention in the complex cascade of events resulting in restenosis. The use of the polymeric forms of nitric oxide described by Keefer et al. provides not only a multivalent approach to treating the restenosis itself, but also provides the controlled delivery of the nitric oxide in amounts and at times appropriate to maximize the effectiveness of the delivered nitric oxide.

SUMMARY OF THE INVENTION

There are certain drugs useful in treating cardiovascular disorders and also potentially useful in prophylactically and/or therapeutically treating restenosis which contain at least one primary and/or secondary amino group and thus are capable of forming NO complexes. Thus, one aspect of the present invention is to develop compounds which can, under physiological conditions, release NO and a corresponding cardiovascular amine in vivo to provide dual activity.

Another aspect of the present invention is to provide methods of treating cardiovascular disorders using the NO cardiovascular amine complexes herein disclosed, and to provide pharmaceutical compositions which contain an effective amount of such complexes.

Still another aspect of the present invention is to provide methods of prophylactically and/or therapeutically treating restenosis using NO cardiovascular amine complexes herein disclosed, and pharmaceutical compositions adapted therefor.

Accordingly, the present invention is a compound of the formula

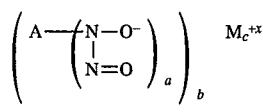

wherein:
A is a cardiovascular amine moiety having at least one secondary or primary amine group;
$M^{+x}$ is a pharmaceutically acceptable cation, wherein x is the valence of the cation;
a is at least one;
b and c are the smallest integers that result in a neutral compound, and wherein the compound under physiological conditions is capable of releasing NO and a cardiovascular amine of the formula AH.

A second aspect of the present invention is a dual acting cardiovascular pharmaceutical composition comprising an effective amount of a compound of the formula I, and a pharmaceutically acceptable carrier, said composition being capable of releasing under physiological conditions NO and a corresponding cardiovascular drug, and a method of treating cardiovascular disorders by administering the above pharmaceutical composition to a host in need thereof.

Preferred among the above NO cardiovascular amine complexes are those derived from known active cardiovascular agents having amino groups available for complexing such as arginine, angiopeptin, heparin, hirudin and a peptide with an RGD sequence.

These preferred compounds as NO complexes are capable of prophylactically and/or therapeutically treating restenosis when releasing under physiological conditions in a host in need thereof effective amounts of NO and the particular cardiovascular amine.

DETAILED DESCRIPTION OF THE INVENTION

By A being a cardiovascular amine moiety is meant that A is any known compound, having at least one primary or secondary amino group, with known therapeutic properties for treating cardiovascular disorders and that when reacted with NO will form a complex which, under physiological conditions, releases NO and its precursor, the cardiovascular amine.

By physiological conditions is meant the chemical, physical and biological conditions found in the body at the point of administration or after distribution of the compound in the bloodstream by any means, direct or indirect. Since the compounds are mostly used intravenously, they should be at least somewhat soluble in aqueous solution, with, if necessary, the help of solubilizing agents or bioacceptable organic solvents.

By at least one primary or secondary amino group is meant a compound having one or more primary or secondary amino groups or mixtures thereof that are capable of reacting with NO to form the derived complex and having the desired therapeutic properties. Compounds having both primary and secondary amino groups will form complexes where the $N_2O_2^-$ group is formed preferably on the secondary amino group.

By pharmaceutically acceptable cation is meant any cation that does not render the compound unstable or insoluble in water or toxic at the doses contemplated; these cations are well known to one of ordinary skill in the pharmaceutical arts. Generally the cation will be a group 1 or group 2 ion, such as sodium, potassium, calcium or magnesium ions, or $NR_2R_3R_4R_5^+$, wherein $R_2$, $R_3$, $R_4$ and $R_5$ are independently selected from the group consisting of H, $C_1-C_4$ alkyl, $C_5-C_6$ cycloalkyl, benzyl or phenyl. The most preferred cations are $Na^+$, $K^+$, $Ca^{+2}$, $Mg^{+2}$, and $NH_4^+$.

The subscripts b and c in formula I mean the number of the particular ion to be found in the empirical formula of the salt. The smallest whole number that results in an electrically neutral compound is used. Thus, if the anion is $ON_2O_2^{-2}$ and the cation is $Na^+$ then b is 1 and c is 2.

In order to prepare compounds of the present invention, the appropriate cardiovascular amines are obtained first and then reacted with NO under suitable conditions to give the derived compounds. Since the cardiovascular amines are well known, they may be purchased from commercial sources or prepared according to well known methods.

The NO cardiovascular amine complexes of the present invention are obtainable by reacting suitable cardiovascular amines with NO in a method similar to that taught by R. S. Drago et al., *J. Am. Chem. Soc.*, Vol. 83, p. 1819–1822 (1961). Drago's method, if used to prepare the inventive compounds herein disclosed, would entail bubbling NO into a cold solution ($\approx -78°$ C.) of the appropriate amine and allowing the formed product to precipitate. Alternatively, high pressure techniques are also taught by R. S. Drago in the cited reference for forming nitric acid adducts, and the same are generally applicable herein. During formation of the NO complexes herein taught, it is noted that only one $N_2O_2^-$ group attaches to each molecule regardless of the number of nitrogen atoms present on the chosen amine. This is due to the fact that the NO adduct salt immediately precipitates upon formation, and is thus not available for further reaction with the NO under either method taught by Drago et al.

Once the desired NO adduct according to the present invention has been prepared, a pharmaceutically acceptable salt thereof, as defined herein, may be prepared if desired. Exemplary of techniques used to prepare such salts would be the preparation of the potassium salt of one of the Formula I compounds herein disclosed by reacting the same with potassium hydroxide in an ethanol or similar solution. Similarly, the sodium, calcium and magnesium salts, among others, could be prepared.

Due to their chemical structures, the compounds of the present invention are preferably administered intravenously and are made into pharmaceutical compositions by combination with appropriate pharmaceutically acceptable carriers or diluents. For example, Formula I compounds provided herein may be formulated into injectable preparations in ways usual for such a route of administration, and the following methods and excipients are exemplary of such usual and acceptable means. Even so, the following should not be considered to limit the scope of the present invention with respect to pharmaceutical compositions or routes of administration.

The compounds of the present invention may be formulated into preparations for injection by dissolving, suspending, or emulsifying them in an aqueous or nonaqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives. Parenteral administration of the compounds of the present invention may also be had by a pharmaceutically acceptable carrier such as dextrose, sterile water for injection, USP, or by normal saline.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The amount of the compounds of the present invention to be used as cardiovascular agents, of course, varies according to the compounds administered, the type of cardiovascular disorder encountered and the route of administration chosen. A suitable dosage is thought to be about 0.01 to 10.0 mg/kg of body weight/day, where one is treating hypertension, arteriosclerosis, cerebral vasospasm or coronary vasospasm and the route of administration is intravenous. The preferred dosage is, of course, that amount just sufficient to treat a particular cardiovascular disorder and would preferably be an amount from about 0.05 to 5.0 mg/kg of body weight/day.

The present invention also provides methods for the prophylactic and therapeutic treatment of restenosis and related disorders in a mammal. The prophylactic method involves the localized administration to a mammal, in particular a human, of a cardiovascular amine NO complex by delivery means comprising a prophylactically effective amount of a polymeric composition comprising a polymer and a cardiovascular amine NO complex bound to the polymer and capable of releasing nitric oxide and the cardiovascular amine to a site in the mammal at risk for restenosis or a related disorder. The therapeutic method involves the localized administration of the complex by delivery means comprising a therapeutically effective amount of the polymeric composition to a site already affected by restenosis or a related disorder. Localized administration means administration at or near the site at risk for or affected by restenosis or related disorder. Delivery means encompasses the manly forms in which the cardiovascular amine NO releasing polymeric composition may be administered, such as vascular implant, stent, heart valve, suture, drug pump, catheter, weeping balloon, and vascular adhering means as described more fully below. Prophylactically and therapeutically effective amounts are as described below with respect to dosages. Whether or not a particular mammal is at risk for restenosis or a related disorder may be determined by gender and previous medical history, e.g., presence of diabetes mellitus, continued smoking, presence of unstable or variant angina pectoris, hypercholesteremia and presence of a previous myocardial infarct as is well-known to those of ordinary skill in the art. Similarly, whether or not a particular mammal is affected by restenosis or a related disorder may be determined by the number and type of vessel(s) affected, position inside the vessel (proximal or distal), and complexity of the original stenosis (length, degree of occlusion, eccentricity of lesion, ostial locations, degree of calcification), as is known in the art. The present invention also provides various delivery means for use in the present prophylactic and therapeutic methods as described more fully below.

The present invention is predicated on the discovery that useful pharmacological agents can be provided by incorporating a cardiovascular amine NO complex into a polymeric matrix. Accordingly, the complex is "bound to the polymer" as that term has been defined herein. It has been discovered that incorporation of the complex into a polymeric matrix provides a polymer-bound cardiovascular amine NO complex composition that can be applied with specificity to a biological site of interest. Site-specific application of the polymer-bound adduct composition enhances the selectivity of action NO and the cardiovascular amine. If the complexes attached to the polymer are necessarily localized, then the effect of their release will be concentrated in the tissues with which they are in contact. If the polymer is soluble, selectivity of action can still be arranged, for example, by attachment to or derivatization of an antibody specific to the target tissue, such as fibrin or tissue thromboplastin.

Additionally, incorporation of the complexes into a polymer matrix can reduce the propensity of the cardiovascular amine NO complex for the relatively rapid release of the dual agents. This prolongs the release of NO and the cardiovascular agent, and allows for efficient dosing to achieve a desired biological effect so the frequency of dosing can be reduced.

While not being bound to any particular theory, it is believed that longevity of drug release in the polymer-bound cardiovascular amine NO complex compositions of the present invention is to be attributed both to the physical structure of the composition and to electrostatic effects. Thus, it is believed that if the polymer is an insoluble solid, the dual acting drug complex near the surface of the particle should be available for rapid release while one that is more deeply imbedded is sterically shielded, requiring more time and/or energy for the dual agent to work its way into the medium. Unexpectedly, it has been found that increasing positive charge in the vicinity of an $N_2O_2^-$ functional group also tends to increase the halflife of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$-catalyzed decomposition.

The nitric oxide-releasing $N_2O_2^-$ functional groups of the cardiovascular amine NO complex that are bound to the polymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide releasing $A[N(O)NO]^-$ group in the vicinity of the particular cells of interest. As an example, covalent attachment of a protecting group to the anionic $[N(O)NO]^-$ function provides a means of postponing nitric oxide release until the molecule reaches an organ capable of metabolically removing the protecting group. By choosing a protecting group that is selectively cleaved by enzymes specific to a tumor, biological disorder, cell, or tissue of interest, for example, the action of the nitric oxide/cardiovascular amine complex can be targeted to maximize the desired effect. While the polymer-bound cardiovascular amine NO complex compositions of the present invention are capable of releasing nitric oxide and the cardiovascular drug in an aqueous solution, such a compound preferably releases nitric oxide and the cardiovascular drug under physiological conditions.

Any of a wide variety of polymers can be used in the context of the present invention. It is only necessary that the polymer selected is biologically acceptable. Illustrative of polymer suitable for use in the present invention are polyolefins, such as polystyrene, polypropylene, polyethylene, polytetrafluorethylene, polyvinylidene difluoride, and polyvinylchloride, polyethylenimine or derivatives thereof, polyethers such as polyethyleneglycol, polyesters such as poly(lactide/glycolide), polyamides such as nylon, polyurethanes, biopolymers such as peptides, proteins, oligonucleotides, antibodies and nucleic acids, starburst dendrimers, and the like.

The physical and structural characteristics of the polymers suitable for use in the present invention are not narrowly critical, but rather will depend on the end use application. It will be appreciated by those skilled in the art that where the polymer-bound nitric oxide/nucleophile adduct compositions of the present invention are intended for local, relatively short term administration or similar administration, they need not be biodegradable. For some uses, such as postangioplasty, coronary bypass surgery or intimal hyperplasia associated with vascular graft implants or the like, it may be desirable that the polymer of the polymer-bound compositions slowly dissolve in a physiological environment or that it is biodegradable.

The polymer-bound nitric oxide releasing compositions may be administered in a wide variety of forms of delivery means. Any delivery means should adequately protect the integrity of the nitric oxide prior to its release and should control the release of the nitric oxide at such at rate, in such an amount, and in such a location as to serve as an effective means of preventing or treating restenosis. For example, delivery means for local administration includes, but are not limited to, sutures, vascular implants (endoluminal, periadventitial), stents, heart valves, drug pumps, drug-delivery catheters (pressure-driven, iontophoretic), self-adhering means (vessel coatings) such as endoluminal implants, liposomes, microparticles, microspheres, beads, disks or other devices. Delivery means for systemic administration include, but are not limited to, solutions, suspensions, emulsions, capsules, sachets, tablets, dermal (topical) patches, lozenges, aerosols, liposomes, microparticles, microspheres, beads including prodrugs, such as a cholesterol acid prodrug, for release into a vascular lesion, tissue-specific antibodies, such as fibrin or tissue thromboplastin, and small peptides that mimic cellular recognition sequences and sequence-specific oligonucleotides as described above. The polymer may itself be structurally sufficient to serve as a form of delivery means. Alternatively, the polymer-bound composition may be incorporated into or coated onto other matrices, substrates or the like, or it may be microencapsulated, or the like.

The complexes of the present invention may be bound to the polymer support in a number of different ways. For example, the compounds described above may be bound to the polymer by coprecipitation of such compounds with the polymer. Coprecipitation involves, for example, solubilizing both the polymer and the cardiovascular amine NO compound and evaporating the solvent.

Since the Formula I compounds release both NO and a known cardiovascular amine in vivo, the preferred dosage is also affected or influenced by the prescribed dosage range for the selected cardiovascular amine used for the NO complex.

Two advantages of the present complexes are the simultaneous administration and dual release of two active agents without producing a residue or ghost, or multiple inactive fragments. In addition by choosing a known and approved cardiovascular amine, toxicity concerns are eliminated.

Particularly preferred cardiovascular amines capable of forming NO complexes are, for example, arginine, angiopeptin, heparin, hirudin or a peptide with an RGD sequence.

Arginine in its physiologically active form is the isomer having the L(+) configuration and of the formula

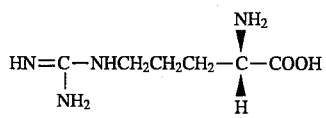

L-arginine has been attributed as being the physiological precursor for the formation of NO in vascular tissue. NO is involved in the control of vascular tone. In rabbit aortic rings, $N^G$-monomethyl-L-arginine (L-NMMA) induces a small but significant endothelium-dependent contraction and inhibits the relaxation and the release of NO induced by acetylcholine. L-arginine, which on its own, only induces a small endothelium-dependent relaxation, antagonizes all the actions of L-NMMA. These results clearly indicate that there is, in the vasculature, a continuous utilization of the L-arginine for the generation of NO which plays a role in the maintenance of blood pressure. See Moncada, S., Palmer, R. M. J., Higgs, E. A. "Biosynthesis of Nitric Oxide From L-Arginine. A Pathway for the Regulation of Cell Function and Communication", *Biochemical Pharmacology* 38:1709–1715, 1989. See also Radomski, M. W., Palmer, R. M. J., Moncada, S., "An L-Arginine/Nitric Oxide Pathway Present in Human Platelets Regulates Aggregation". *Proco Natl. Acad. Sci. USA*, 87:5193–5197, 1990.

Angiopeptin, a cyclic octapeptide analog of somatostatin, markedly inhibits myointimal proliferation in response to endothelium cell injury in rat carotid artery, rabbit aorta and iliac arteries and in coronary arteries of transplanted rabbit hearts. This activity suggests its use in preventing, reversing and/or modifying restenosis after percutaneous transluminal coronary angioplasty and in preventing accelerated coronary atherosclerosis after cardiac transplantation. See Conor F. Lundergan, MD, Marie L. Foegh, MD, Peter W. Ramwell, MD "Peptide Inhibition of Myointimal Proliferation by Angiopeptin, a Somatostatin Analogue", *Journal of the American College of Cardiology*, 17:132B-6B (1991), J. V. Conte, M. L. Foegh, D. Calcagno, R. B. Wallace and P. W. Ramwell, "Peptide Inhibition of Myointimal Proliferation following Angioplasty in Rabbits", Proceedings of the Fifth International Workshop on Aspiration Cytology and Other Noninvasive Methods of Diagnosis of Rejection in Transplantation, Mar. 27–29, 1989, pages 3686–3688, and Clemmon, D. R., VanWyk, J. J., "Evidence for a Functional Role of Endogenously Produced Somatomedinlike Peptides in the Regulation of DNA Synthesis in Cultured Human Fibroblasts and Procine Smooth Muscle Cells", *J. Clin. Invest.*, 75:1914–18, 1985.

Heparin, known also as glycosaminoglycan, has anticoagulant activity and comprises a heterogeneous mixture of various sulfated polysaccharide chains composed of repeating units of D-glucosamine and either L-iduronic or D-glucuronic acids having a molecular weight range from 6,000 to 30,000 Daltons. Heparin is well known as an antithrombotic or anticoagulant. It has also been reported to be useful in suppressing smooth muscle cell proliferation in injured arteries, see Clowes, A., Karnovsky, M., "Suppression by Heparin of Smooth Muscle Cell Proliferation Injury", *Nature* 285:623–625, 1977. Guyton, J., et al. in *Cir. Res.*, 46:625–634, 1980.

Another anticoagulant is hirudin, which is a polypeptide with a molecular weight of about 10,800 based on amino acid composition. Hirudin is characterized by a high proportion of dicarboxylic acids, which explains its acid character, and by the absence of tryptophan, methionine and arginine. Hirudin and heparin have been recently reported to be active as thrombin inhibitors on a development of acute platelet thrombus deposition during angioplasty in pigs, Heras, M., et al. *Circulation* 79:657–685, 1989.

A peptide having RGD sequence, (Arg-Gly-Asp) has also been linked to the regulation proliferation of arterial smooth muscle cells. Thyberg, J., et al. *Arteriosclerosis*, 10:966–980 1990.

The above particularly identified cardiovascular agents are cardiovascular amines that contain at least one or more primary or secondary amino groups and would be capable of forming NO complexes. Release of these agents would not only provide the benefits of NO, but also the particular cardiovascular benefits of the cardiovascular amine per se.

Examples of Systemic Delivery of Cardiovascular Amine NO Complexes:

1. Injection (intravenous, intraperitoneal)—Prepare a stock solution of NO complex by weighing an appropriate amount of NO complex into a volumetric flask. For example, for a $10^{-2}$M solution, weigh 0.01 mol. of a cardiovascular amine NO complex into a 10-mL volumetric flask. Dissolve in a few ml ice-cold 10 mM NaOH, then make to volume with ice-cold 10 mM NaOH; keep on wet ice. From this stock solution, prepare dosing solutions with an excess of phosphate-buffered saline (PBS), pH 7.4. For example, to prepare a $10^{-5}$M dosing solution, dilute 10 µL of $10^{-2}$M stock solution 1:1000, i.e., to 10 mL with ice-cold PBS. This dosing solution can then be used to provide a single dose or a continuous infusion to mammals, e.g., continuously infuse 1–2 µg/Kg/min for 5 minutes to lambs or a single daily intravenous injection of 10 µg/Kg to pigs.

2. Transdermal—Dissolve the NO complex in enough ice-cold 10% distilled water in propylene glycol to provide the proper dosing concentration, e.g., 5 µmol. Apply 0.2 mL of the solution to a shaved area of skin three times per week. Alternatively, the NO complex can be dissolved in ice-cold distilled water and then diluted 10-fold with cold propylene glycol and applied as before.

Examples of Local Delivery of Cardiovascular Amine NO Complexes:

(Advantages of local delivery are (1) ability to attain effective concentrations of drug at the target site more quickly than systemic administration, (2) less dose required with local delivery than with systemic delivery and (3) fewer toxic effects observed with the local delivery compared to those observed with the systemic delivery).

1. Porous membrane/iontophoretic delivery—NO complex is dissolved in water and maintained icecold. A balloon catheter constructed of a microporous membrane, e.g., 150 Å polycarbonate membrane (Nucleopore®, Costar Corporation, Cambridge, Mass. or Fluoropore®, Millipore Corporation, Bedford, Mass.) is inserted into the blood vessel at the site of angioplasty. The NO complex solution is used to inflate the balloon at the site of injury. An electrical current (e.g., 5 mA, 8–10 V) is passed through the balloon for 1–2 minutes. During this time, 100–3000 µg NO adduct is transferred through the balloon into the vessel wall.

2. Biodegradable polymer—In small increments with gentle stirring, add polyoxypropylenepolyoxyethylene block co-polymer (Pluronic® F127 NF, BASF Corporation, Parsippany, N.J.) to ice-cold water or phosphate buffered saline, pH 7.4, to make a 25% by weight solution. The appropriate amount of NO complex to provide the needed dosage is contained in the water or phosphate buffered saline. This results in a clear solution, a portion of which, e.g., 0.2 mL, can be added around the outside of an injured vessel, e.g., to a balloon injured rat carotid artery, just prior to closing the wound. The resulting gel delivers the cardiovascular amine and the NO over a period of several hours to a few days.

3. Biodegradable in situ formed polymer (ATRIGEL™, ATRIX Laboratories, Fort Collins, Colo.)—In N-methyl-2-pyrollidone containing the requisite amount of NO complex, dissolve with stirring enough dry biodegradable polymer(s) to result in a 50% solution of polymer by weight. Polymers which can be used include, e.g., poly(DL-lactide); 75/25, poly(DL-lactide-co-glycolide); 50/50, poly(DL-lactide-co-caprolactone). The resulting solution gels when it comes into contact with water, e.g., in a body cavity. A portion of this solution, e.g., 0.2 mL, can be injected around the area of vessel injury. After the solution gels, drug is eluted from this system over a period of days or weeks, depending on the polymer system used.

What is claimed is:

1. A compound of the formula

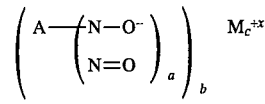

wherein:

A is a cardiovascular amine moiety derived from a compound selected from the group consisting of angiopeptin, heparin and hirudin;

$M^{+x}$ is a pharmaceutically acceptable cation, wherein x is the valence of the cation;

a is at least one;

b and c are the smallest integers that result in a neutral compound, and wherein the compound under physiological conditions is capable of releasing NO and a cardiovascular amine of the formula AH.

2. A compound according to claim 1 wherein the compound is capable of releasing angiopeptin.

3. A compound according to claim 12 wherein the compound is capable of releasing heparin.

4. A compound according to claim 1 wherein the compound is capable of releasing hirudin.

5. A dual acting cardiovascular pharmaceutical composition comprising an effective amount of a compound of the formula

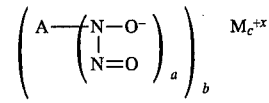

according to claim 1, and a pharmaceutically acceptable carrier, said composition being capable of releasing under physiological conditions NO and a corresponding cardiovascular drug.

6. The composition of claim 5 wherein the effective amount of the compound is the established dose range of the cardiovascular drug to be released with NO.

7. A method of treating cardiovascular disorders which comprises administering to a host in need thereof a dual activity cardiovascular composition of claim 5.

8. A method of prophylactically or therapeutically treating restenosis which comprises administering to a host in need thereof a prophylactic or therapeutic effective amount of a dual activity pharmaceutical composition of claim 5.

* * * * *